United States Patent [19]

Hechenbleikner et al.

[11] Patent Number: 4,511,725

[45] Date of Patent: Apr. 16, 1985

[54] PREPARATION OF N-ACYL-2,5-DIMETHYLPYRROLES FROM AMIDES AND ACETONYLACETONE

[75] Inventors: Ingenuin Hechenbleikner, West Cornwall; William P. Enlow, Falls Village, both of Conn.

[73] Assignee: Borg-Warner Chemicals, Inc., Parkersburg, W. Va.

[21] Appl. No.: 458,603

[22] Filed: Jan. 17, 1983

[51] Int. Cl.$^3$ .......................................... C07D 207/327
[52] U.S. Cl. ................................. 548/530; 548/539; 548/540
[58] Field of Search ......................... 548/530, 539, 540

[56] References Cited

U.S. PATENT DOCUMENTS

| | | | |
|---|---|---|---|
| 2,453,671 | 11/1948 | Sargent | 548/536 |
| 2,453,675 | 11/1948 | Sickels et al. | 548/536 |
| 2,453,676 | 11/1948 | Sickels | 548/536 |
| 2,464,770 | 3/1949 | Sargent | 548/536 |
| 2,859,833 | 11/1958 | Nelson | 548/540 |

OTHER PUBLICATIONS

Jones, et al., "The Chemistry of Pyrroles", (1977), Academic Press (N.Y.), p. 77.
C.A. 8th Coll. Index, Subject Index, pp. 268335–268345, (1973).
Jones, et al., C.A.; 68, (1968), 12255d.
Sano, et al., C.A.; 88, (1978), 186329j.
Moon, et al., C.A.; 80, (1974), 82554x.
Young, et al., Organic Synthesis, Collective vol. 2, pp. 219–220, (1943).
C.A.; 56, (1962), Neugebauer et al., 8214–8216.

Primary Examiner—Joseph Paul Brust
Attorney, Agent, or Firm—Richard J. Schlott

[57] ABSTRACT

N-acyl-2,5-dimethylpyrroles and a process for their preparation. The process involves heating a mixture of acetonylacetone and an amide. The ensuing reaction is a condensation reaction with water being split out.

5 Claims, No Drawings

PREPARATION OF N-ACYL-2,5-DIMETHYLPYRROLES FROM AMIDES AND ACETONYLACETONE

This invention relates as indicated to N-acyl-2,5-dimethylpyrroles and more particularly to a process for the preparation of such compounds.

BACKGROUND OF THE INVENTION

The substituted pyrroles of this invention are useful as intermediates in the syntheses of polymer additives which in turn are effective to protect various polymers from deterioration caused by exposure to ultraviolet light. The substituted pyrroles can be reacted with acetylene dicarboxylic acid, in a Diels-Alder reaction,

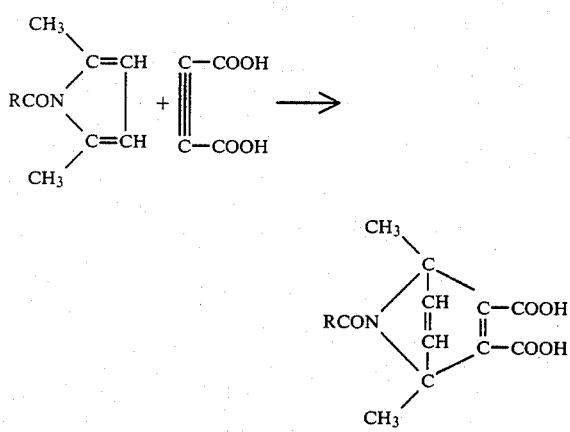

for example, to form a azanorbornadiene compound which is effective to inhibit the deterioration of polypropylene upon exposure to ultraviolet light. Hydrogenation of such a azanorbornadiene to the corresponding norbornane yields a similarly effective ultraviolet light stabilizer, i.e., the azanorbornane. Other active dienophiles may of course also be used for this purpose, and illustrative examples include diethylacetylene dicarboxylate, propargyl alcohol and butynediol.

The effectiveness of these Diels-Alder reaction products as light stabilizers is believed to be due to the hindered amide group.

Also, the acyl groups may be removed (by hydrolysis) from these Diels-Alder condensation products and the resulting hindered amines likewise are effective ultraviolet light stabilizers in polymer compositions.

While a wide variety of polymers are benefited by the protective action of these Diels-Alder products, olefin polymers are especially benefited. Polypropylene, in particular, is susceptible to stabilization by the addition of a small proportion of such an additive.

The condensation of gamma-diketones such as hexane-2,5-dione, i.e., acetonylacetone, with primary amines to form pyrroles, is shown at page 77 of "The Chemistry of Pyrroles" by Jones et al., Academic Press (1977). The reaction is referred to as the Paal-Knorr condensation. It appears that the condensation reactions were carried out in aqueous systems because there is a considerable discussion about the optimum pH at which the reaction may be carried out. Moreover, it is stated that 2,5-dimethylpyrrole may be prepared from the reaction of hexane-2,5-dione and formamide; such a result was obtained in an aqueous environment.

SUMMARY OF THE INVENTION

The invention here is an N-acyl-2,5-dimethylpyrrole having the molecular structure

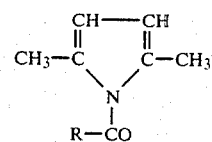

where R is hydrogen, alkyl of 1–19 carbon atoms, or phenyl. The invention also includes a process for preparing such N-acyl-2,5-dimethylpyrroles comprising reacting acetonylacetone with an amide. The process is illustrated by the following equations:

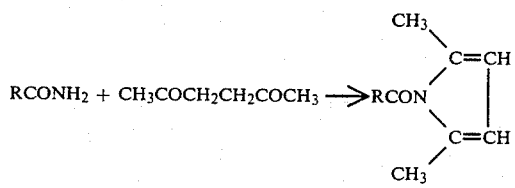

DETAILED DESCRIPTION OF THE INVENTION

R in the above structure may, as indicated, be hydrogen, phenyl or alkyl. The alkyl group may contain 1–19 carbon atoms. Illustrative examples of such R groups include methyl, ethyl, n-propyl, n-heptyl, n-nonyl, n-decyl, n-octadecyl, etc.

It will be noted that the amide group of the composition of the invention is hindered by the two methyl groups in the 2- and 5-positions. It is believed that such hindrance is a factor in the notable effectiveness as light inhibitors of the Diels-Alder products which may be prepared from these substituted pyrroles.

The process of the invention is carried out in an anhydrous system. In some instances, to insure the substantial absence of water, it is advisable to heat, at reflux temperature, a solution of the amide in a water-immiscible solvent such as toluene, collecting any water in a Dean-Stark trap. Then, when no more water is thus collected, acetonylacetone is added and the whole is heated until the reaction is complete.

The process requires the reaction of one mol of amide per one mol of acetonylacetone and, generally, these are the proportions of reactants that should be used for a most efficient reaction. The use of a substantial excess of either reactant merely results in the loss of the excessive amount of that reactant.

A catalyst ordinarily is used. Acidic catalysts are preferred. Illustrative examples of suitable acidic catalysts include p-toluenesulfonic acid, methanesulfonic acid, sulfonic acid, phosphoric acid, cationic resins such as sulfonated copolymers of butadiene and styrene, dilauryl phosphoric acid and the like.

It is desirable to use a solvent. Among other reasons, it facilitates removal of water, as it is formed, from the reaction mixture, viz., by means of a Dean-Stark trap. Water-insoluble solvents should be used. Toluene, benzene, xylene, heptane, tetrachloroethane and chlorobenzene are illustrative. The boiling point of the solvent may range from about 75° C. to about 200° C., although a narrower range is preferred so as to permit easy removal (at a lower temperature) of the solvent from the product mixture, i.e., from about 100° C. to about 140° C.

The process is carried out quite simply; the reaction mixture is heated at a temperature within the range of from about 75° C. to about 200° C., usually at the reflux temperature of the solvent. Water is removed from the product mixture as it is formed and when no more water is formed the reaction is halted. The N-acyl-2,5-dimethylpyrrole product is isolated by distillation. The distillate usually comprises a mixture of the desired pyrrole and a small proportion of unreacted acetonylacetone. This latter can be removed by extraction with a solvent such as heptane; i.e., one which dissolves acetonylacetone more readily than the substituted pyrrole.

EXAMPLE 1

A solution of 59 g. (1.0 mol) of acetamide, 110 ml. (107 g., 0.94 mol) of acetonylacetone and 0.5 g. of p-toluenesulfonic acid in 200 ml. of toluene is heated at reflux temperature for 18 hours, during which time 28 ml. (1.75 mol) of water is collected in a Dean-Stark trap. The mixture is allowed to cool and then is filtered to yield 16 g. of solid acetamide. The filtrate is concentrated to a liquid residue which is distilled yielding 32 g. of a clear liquid product boiling at 90°-95° C./20 mm. Gas chromatographic analysis shows it to contain 96% of the desired product, i.e., N-acetyl-2,5-dimethyl-pyrrole.

EXAMPLE 2

A solution of 90.0 g. (2.0 mol) of formamide, 114 g. (1.0 mol) of acetonylacetone and a trace of p-toluenesulfonic acid in 50 ml. of benzene is heated at reflux temperature for 67 hours during which time 14.5 ml. (0.8 mol) of water is collected in a Dean-Stark trap. The product mixture is concentrated and the liquid residue distilled at 20 mm. yielding 153.1 g. of distillate. This distillate is extracted with 150 ml. of heptane and the heptane extract distilled to yield 25.0 g. of distillate boiling at 90°-95° C./20 mm. Gas chromatographic analysis shows it to contain 80% of the desired product, N-formyl-2,5-dimethylpyrrole. The residue (from the heptane extraction) is extracted again with another 75 ml. of heptane and the heptane extract distilled to yield 14.8 g. of distillate which is shown by gas chromatographic analysis to contain 50% of desired product.

EXAMPLE 3

A solution of 90 g. (0.75 mol) of benzamide, 87.6 g. (0.77 mol) of acetonylacetone and 0.5 g. of p-toluenesulfonic acid in 200 ml. of toluene is heated at reflux temperature for 29 hours, collecting 16 ml. of water in a Dean-Stark trap during this period. The product mixture is distilled and the distillate stirred with 200 ml. of heptane and filtered. The heptane is evaporated from the filtrate and the residue is shown, by infrared analysis, to contain C=O groups but no NH groups. It is presumed to be N-benzoyl-2,5-dimethylpyrrole.

All parts and percentages herein are by weight unless otherwise clearly stated.

We claim:

1. A process for preparing N-acyl-2,5-dimethylpyrroles comprising mixing acetonylacetone with a 1–20 carbon atom carboxamide selected from the group consisting of formamide, alkylcarboxamides and phenyl carboxamide and a non-aqueous, water-immiscible solvent, heating the resulting mixture at a temperature in the range 75° to 200° C. in the presence of an acid catalyst and removing water from the mixture, and isolating said N-acyl-2,5-dimethylpyrroles.

2. The process of claim 1 wherein the carboxamide is an alkyl carboxamide containing 1–20 carbon atoms.

3. The process of claim 1 wherein the mixture of N-acyl-2,5-dimethylpyrrole and acetonylacetone is substantially anhydrous.

4. The process of claim 3 wherein the carboxamide is acetamide.

5. The process of claim 3 wherein the carboxamide is phenyl carboxamide.

* * * * *